United States Patent
Seibert et al.

(10) Patent No.: US 7,229,785 B2
(45) Date of Patent: Jun. 12, 2007

(54) FLUORESCENCE TECHNIQUE FOR ON-LINE MONITORING OF STATE OF HYDROGEN-PRODUCING MICROORGANISMS

(75) Inventors: Michael Seibert, Lakewood, CO (US); Valeriya Makarova, Golden, CO (US); Anatoly A. Tsygankov, Pushchino (RU); Andrew B. Rubin, Moscow (RU)

(73) Assignee: Midwest Research Institute, Kansas City, MO (US)

( * ) Notice: Subject to any disclaimer, the term of this patent is extended or adjusted under 35 U.S.C. 154(b) by 362 days.

(21) Appl. No.: 10/511,929

(22) PCT Filed: Apr. 19, 2002

(86) PCT No.: PCT/US02/12576

§ 371 (c)(1),
(2), (4) Date: Oct. 18, 2004

(87) PCT Pub. No.: WO03/088736

PCT Pub. Date: Oct. 30, 2003

(65) Prior Publication Data

US 2005/0239044 A1    Oct. 27, 2005

(51) Int. Cl.
    *C12P 1/00*    (2006.01)
(52) U.S. Cl. ...................... 435/41; 435/257.1
(58) Field of Classification Search ............ 435/29, 435/34, 41, 252.1, 257.1, 257.6, 287.5, 288.7, 435/303.2; 47/1.4
See application file for complete search history.

(56) References Cited

U.S. PATENT DOCUMENTS

| | | | |
|---|---|---|---|
| 5,372,784 A | 12/1994 | Morris et al. | |
| 5,700,370 A | 12/1997 | Helmo | |
| 5,965,801 A * | 10/1999 | Layzell et al. | 73/23.2 |
| 5,981,958 A | 11/1999 | Li et al. | |
| 6,107,033 A | 8/2000 | Welling et al. | |
| 6,410,258 B1 | 6/2002 | McTavish | |
| 6,989,252 B2 * | 1/2006 | Melis et al. | 435/168 |
| 2001/0041351 A1 * | 11/2001 | Seibert et al. | 435/34 |
| 2001/0053543 A1 * | 12/2001 | Anastasios et al. | 435/168 |
| 2003/0162273 A1 * | 8/2003 | Melis et al. | 435/168 |
| 2006/0166343 A1 * | 7/2006 | Hankamer et al. | 435/168 |

FOREIGN PATENT DOCUMENTS

DE    19930865    2/2001

OTHER PUBLICATIONS

Boichenko, V. et al., "Simultaneous Measurements of Fluorescence Induction and Light-Induced Hydrogen Evolution in Chorella" Biofizika 1983, 28(6) 976-9.
Serodio, J. et al., "Relationship Between Chlorophyll Fluorescence Quenching and O2 evolution in Microalgae." Photosynthesis: Mechanisms and Effects. vol. V., 4109-4112, Kluwer Academic Publishers, Aug. 17-22, 1998 presented.
Melis, et al. 2000. Plant Physiol V. 122. p. 127-136, "Sustained Photobiological Hydrogen Gas Production Upon Reversible Inactivation of Oxygen Evolution in the Green Alga Chlamydomonas reinhardhii".
Ghirardi et al. 2000, a Trends Biotechnol. V. 18, pp. 506-511, "Microalgae: A Green Source of Renewable H2".

* cited by examiner

Primary Examiner—Ralph Gitomer
(74) Attorney, Agent, or Firm—Paul J. White

(57) ABSTRACT

In situ fluorescence method to monitor state of sulfur-deprived algal culture's ability to produce $H_2$ under sulfur depletion, comprising: a) providing sulfur-deprived algal culture; b) illuminating culture; c) measuring onset of $H_2$ percentage in produced gas phase at multiple times to ascertain point immediately after anerobiosis to obtain $H_2$ data as function of time; and d) determining any abrupt change in three in situ fluorescence parameters; i) increase in $F_t$ (steady-state level of chlorophyll fluorescence in light adapted cells); ii) decrease in $F_m'$ (maximal saturating light induced fluorescence level in light adapted cells); and iii) decrease in $\Delta F/F_m' = (F_m' - F_t)/F_m'$ (calculated photochemical activity of photosystem II (PSII) signaling full reduction of plastoquinone pool between PSII and PSI, which indicates start of anaerobic conditions that induces synthesis of hydrogenase enzyme for subsequent $H_2$ production that signal oxidation of plastoquinone pool as main factor to regulate $H_2$ under sulfur depletion.

16 Claims, 5 Drawing Sheets

Figure 1:
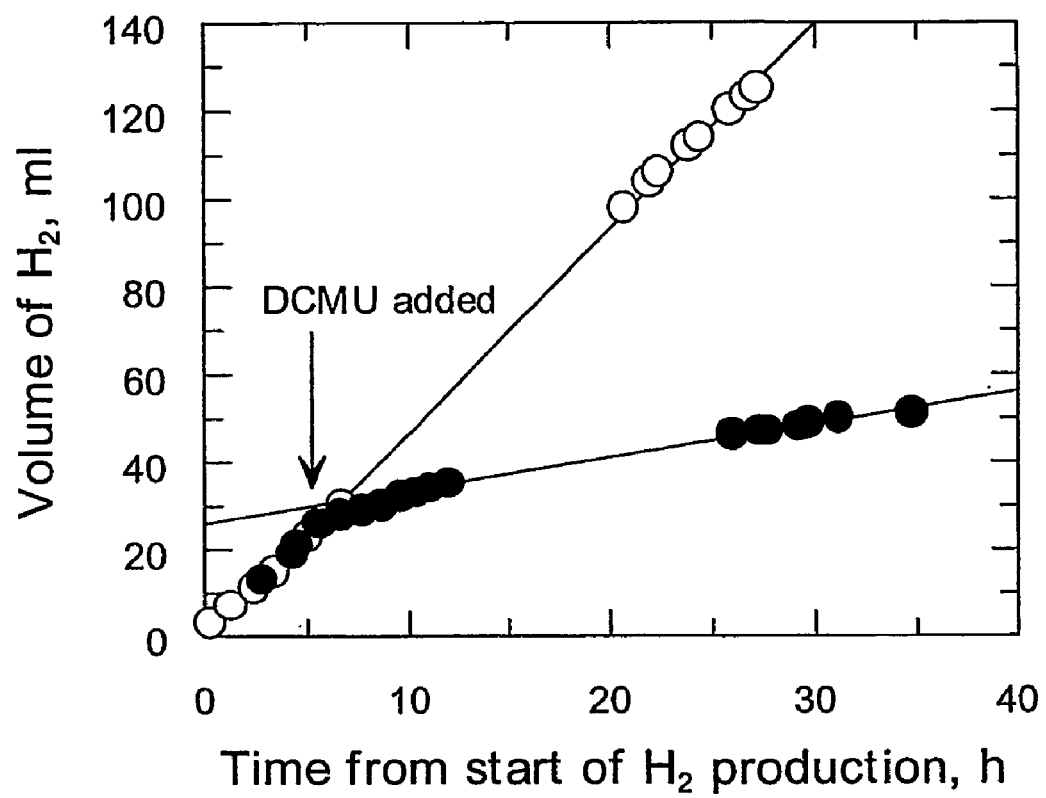

FLUORESCENCE TECHNIQUE FOR ON-LINE MONITORING OF STATE OF HYDROGEN-PRODUCING MICROORGANISMS

CONTRACTUAL ORIGIN OF THE INVENTION

The United States Government has rights in this invention pursuant to Contract No. DE-AC36-99GO10337 between the United States Department of Energy and the Midwest Research Institute.

This application is filed under Rule 371 as a National Stage from PCT/US 02/12576 filed Apr. 19, 2002.

BACKROUND OF THE INVENTION

1. Field of the Invention

The invention relates to providing a non-destructive, external or remote, on-line way to monitor the physiological state of stressed (inclusive of nutrient stress and sulfur-deprivation stress) oxygenic photosynthetic microorganisms that have a hydrogenase in situ with regard to their ability to produce $H_2$ gas without having to rely on electrodes or other sensors placed in direct contact with the culture medium.

2. Description of the Prior Art

The ability of eukaryotic microalgae to produce $H_2$ after a dark, anaerobic induction period was discovered about 60 years ago; however, the enzyme catalyzing this activity, a reversible Fe-hydrogenase, is inactivated by trace amounts of $O_2$ that is co-evolved during photosynthesis. Thus, light-dependent $H_2$ production by green algae, including *Chlamydomonas reinhardtii*, is observed for only a very short period of time after anaerobic induction. Several years ago, Wykoff et al. [1] found that incubating cells deprived of inorganic sulfur for up to 120 h, resulted in the progressive reduction of photosynthetic capacity due to the inactivation of photosystem II (PSII) $O_2$-evolution activity by up to 95%.

1. 1998. *Plant Physiol.* V. 117. P. 129-139.

Subsequent work [Melis et al. [2] and Ghirardi et al. [3],[4] investigated this effect more thoroughly and showed that after 1-2 days of adaptation to sulfur-deprived conditions, *C. reinhardtii* cells could produce volumetric amounts of $H_2$ gas for a few days under continuous illumination. The key observation made was that, when the rate of photosynthetic $O_2$ evolution declined below the rate of cell respiration, the culture could make itself anaerobic. Under these conditions, the hydrogenase enzyme was activated and/or induced in the light, and the onset of $H_2$ production followed after several hours. It has been demonstrated that the process involved the sequential transition through the following five physiological phases: $O_2$-evolution, $O_2$-consumption, anaerobic adaptation, $H_2$-production, and termination phases. After this occurred, the culture could be regenerated by adding sulfate, prior to another round of $H_2$ production. Nevertheless, the actual mechanisms involved in and the time-course for the decrease in PSII activity in sulfur-deprived cells during cell transition to the anaerobic state as well as the role of PSII in $H_2$ are not well established.

2. 2000. *Plant Physiol* V. 122. P. 127-136.
3 2000 a *Trends Biotechnol.* V. 18. P. 506-511
4

U.S. Pat. No. 5,372,784 discloses measurement of bacterial $CO_2$ production in an isolated fluorophore by monitoring an absorbance-regulated change of fluorescence. The fluorophore is positioned to intersect the transmission light path, and indirectly monitors absorbance or changes in the absorbance of a chromophore encapsulated or isolated by a gas permeable polymetric matrix.

A biological treatment plant controlled by fluorescence sensors is disclosed in U.S. Pat. No. 5,700,370. The method of using these fluorescence sensors comprises:

monitoring the microbiological activity of the biological system and/or fluctuations thereof by on-line measurement of fluorescent emission and/or variations therein for at least one characteristic biogenic fluorophore present in the mixed culture of microorganisms in the system when irradiated with light and controlling one or several parameters of the process by using results from the measurement as measured variable(s) in an on-line automatization system.

U.S. Pat. No. 5,981,958 discloses a method and apparatus for detecting pathological and physiological change in plants. This invention provides an imaging fluorometer comprising a source of electromagnetic radiation, optical components to direct the radiation, excitation and emission filters, and an imaging-device. Radiation from the radiation source is used to excite fluorescence from a dark-adapted sample containing photosynthetic components. This fluorescence is collected by the imaging device as a function of time and position within the sample. Excitation and emission filters limit the intensity and wavelengths of radiation incident on the sample and imaging device, respectively.

A method and material for determining relative abundance of microorganisms in fixed populations is disclosed in U.S. Pat. No. 6,107,033. The method entails:

1) providing a set of labeled in situ hybridization cluster oligonucleotide probes;
2) hybridization of said probes with a sample of the mixed population, and
3) quantitative analysis of the number of labeled microorganisms.

German Patent, DE 19930865 discloses methods for detecting phytoplankton content of natural water samples by chlorophyll fluorescence measurements. The measurements allow distinguishment among different algae groups on the basis of chlorophyll fluorescence measurements using a measuring beam in combination with strong pulses of light with different intensities, frequencies, phases, and wavelengths. The system of this patent includes:

a first light source for producing a weak measuring light for exciting fluorescence in a selected portion of the sample volume;

a second light source for illuminating the remaining volume of the sample with a light intense enough to induce phototaxis (e.g., by dinoflagellates);

means for detecting and recording the time-dependent changes in light in the sample volume and the portion of the sample undergoing measurement; and means for comparing the changes to known values.

The time-dependent changes in fluorescence exhibit relative amplitudes and time constants, which are characteristic of certain dinoflagellate types.

Karukstis et al., in *Photochemistry and Photobiology* (1992) Vol. 55. No. 1 pp. 125-132 disclose "*ALTERNATIVE MEASURES OF PHOTOSYSTEM II ELECTRON TRANSFER INHIBITION IN ANTHRAQUINONE-TREATED CHLOROPLASTS*" that compare electron direct transport assays with an indirect fluorescence assay for basic research studies.

An *ON-LINE MONITORING OF CHLOROPHYLL FLUORESCENCEE TO ASSESS THE EXTENT OF PHOTOINHIBITION OF PHOTOSYNTHESIS INDUCED BY OXYGEN CONCENTRATION AND LOW TEMPERATURE AND ITS EFFECT ON THE PRODUCTIVITY OF OUT-

DOOR CULTURES OF SPIRULINA PLATENSIS (CYANOBACTERIA) is disclosed by Torzilla et al. in *J. Phycol.* Vol. 34 (1998) pp. 504-510.

Polle et al. *Biohydrogen II, (workshop)* (2001) Meeting date 1999. pp. 111-130 disclose *MAXIMIZING PHOTOSYNTHETIC EFFICIENCIES AND HYDROGEN PRODUCTION IN MICROALGA CULTURES* by developing algal mutants with smaller antenna sizes.

There is a need for providing a technique for on-line monitoring of the state of hydrogen-producing microorganisms under aerobic and anaerobic conditions inside a closed photobioreactor system from an external vantage point to gain information about the state of the culture without using electrodes inserted directly into the culture medium, and thereby preclude the possibility of a source of (a) culture contamination and the need to sterilize electrodes, and (b) gas, including oxygen and hydrogen, leaks, to produce a non-destructive, remote sensing procedure.

SUMMARY OF THE INVENTION

One object of the present invention is to provide a process for determining the main factor(s) in regulating $H_2$ production under sulfur depletion of oxygenic photosynthetic microorganisms that have a hydrogenase.

Another object of the present invention is to provide a process for determining the main factor(s) in regulating $H_2$ production under sulfur depletion of oxygenic photosynthetic microorganisms that have a hydrogenase, by monitoring the culture from an external vantage point.

A further object of the present invention is to provide a process for determining the main factor(s) in regulating $H_2$ production under sulfur depletion of oxygenic photosynthetic microorganisms that have a hydrogenase, by monitoring the culture from an external vantage point, without using electrodes or other type of sensor inserted directly into the culture medium.

A yet further object of the present invention is to provide a process for determining the main factor(s) in regulating $H_2$ production under sulfur depletion of oxygenic photosynthetic microorganisms that have a hydrogenase, by monitoring the culture free from a source of culture contamination or gas leakage, that remotely senses the culture in a manner that is non-destructive to the sample.

In general, the invention process is accomplished by monitoring the physiological state of sulfur-deprived algal cultures that progress through the physiological phases of: $O_2$ production, $O_2$ consumption, anaerobic adaptation, $H_2$ production, and termination, to ascertain a number of significant and well-defined fluorescence parameter changes during and between these phases; namely, to the effect that, at the exact time that sulfur-stressed algae become anaerobic, the following three in situ fluorescence parameters change dramatically and are used to determine when and if a culture in a photobioreactor goes anaerobic:

$F_t$ (the steady-state level of chlorophyll (Chl) fluorescence in light-adapted cells) increases abruptly;

$F_m'$ (the maximal saturating light-pulse induced fluorescence level in light-adapted cells) decreases abruptly; and $\Delta F/F_m' = F_m' - F_t)/F_m'$ (the calculated photochemical activity of photosystem II [PSII] under steady-state illumination) decreases precipitously and abruptly.

The in situ fluorescence method for on-line monitoring of the state of sulfur-deprived algal culture to ascertain the culture's ability to produce $H_2$ under sulfur depletion entails:

a) providing a sample of sulfur-deprived algal culture containing photosynthetic components;

b) illuminating the sample with artificial or natural illumination;

c) determining the onset of $H_2$ photoproduction by measuring the percentage of $H_2$ in a produced gas phase at multiple times to ascertain the point immediately after the anerobiosis subsequent to the physiological phases of $O_2$ production and $O_2$ consumption sequence to obtain data regarding $H_2$ as a function of time; and d) determining any abrupt change in the following three in situ fluorescence parameters:

i) an abrupt increase in $F_t$ (the steady-state level of chlorophyll fluorescence in light adapted cells);

ii) an abrupt decrease in $F_m$, (the maximal saturating light induced fluorescence level in light adapted cells); and iii) a precipitous and abrupt decrease in $\Delta F/F_m' = (F_m' - F_t)/F_m'$ (the calculated photochemical activity of photosystem II (PSII)) that signal the full reduction of the plastoquinone pool between PSII and PSI, which indicates the start of anaerobic conditions that in turn induces the synthesis of the hydrogenase enzyme required for subsequent $H_2$ production, and thereafter slowing down of the abrupt decrease and partial recovery of $\Delta F/F_m'$ signal at least partial oxidation of the plastoquinone pool as the main factor to regulate $H_2$ production under sulfur depletion.

BRIEF DESCRIPTION OF THE DRAWINGS FIGURES

FIG. 1 is a graph showing the effect of 10 μM DCMU on the rate of $H_2$ photoproduction by cultures of sulfur-depleted *C. reinhardtii* cells, where the control cells are open circles and the DCMU-treated cells, are closed articles. DCMU was added to treated cells at the arrow. Time zero in this case represents the time after $H_2$ photoproduction starts.

Figure 2:
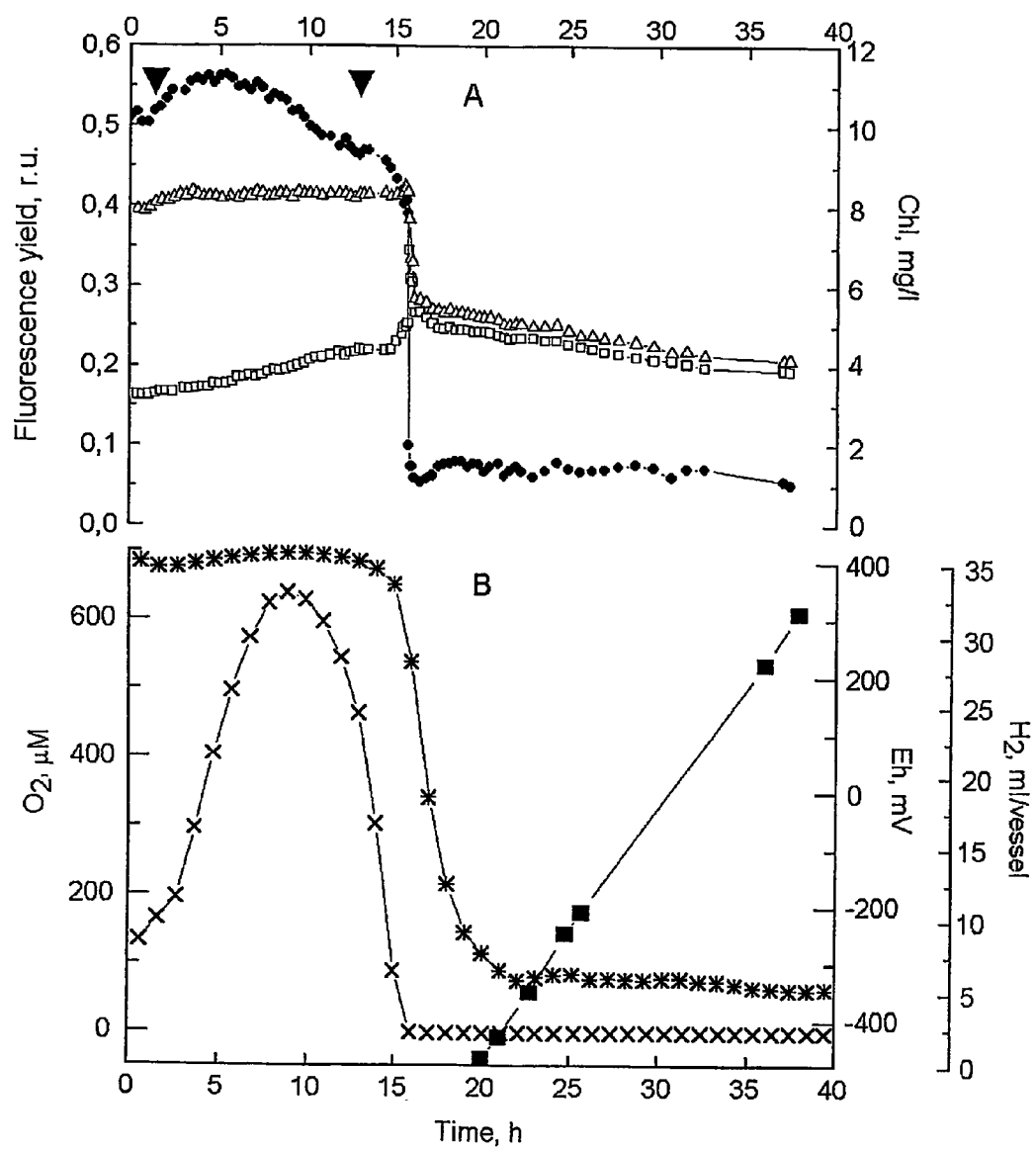

FIG. 2 is a graph of a time course of physiological parameters and $H_2$ production in *C. reinhardtii* cells during incubation under sulfur-deprived conditions. More particularly, FIG. 2A shows in situ fluorescence parameters $F_t$ (open squares), $\Delta F/F_m'$ (solid circles), and $\Delta F_m'$ (open triangles) and chlorophyll concentrations (Chl; solid triangles) as a function of time, and FIG. 2B shows dissolved oxygen ($pO_2$, crosses), redox potential $E_h$ (stars) and $H_2$ gas collected in an inverted graduate cylinder (solid squares). Incubation in sulfur-deprived medium started at 0 h.

Figure 3:
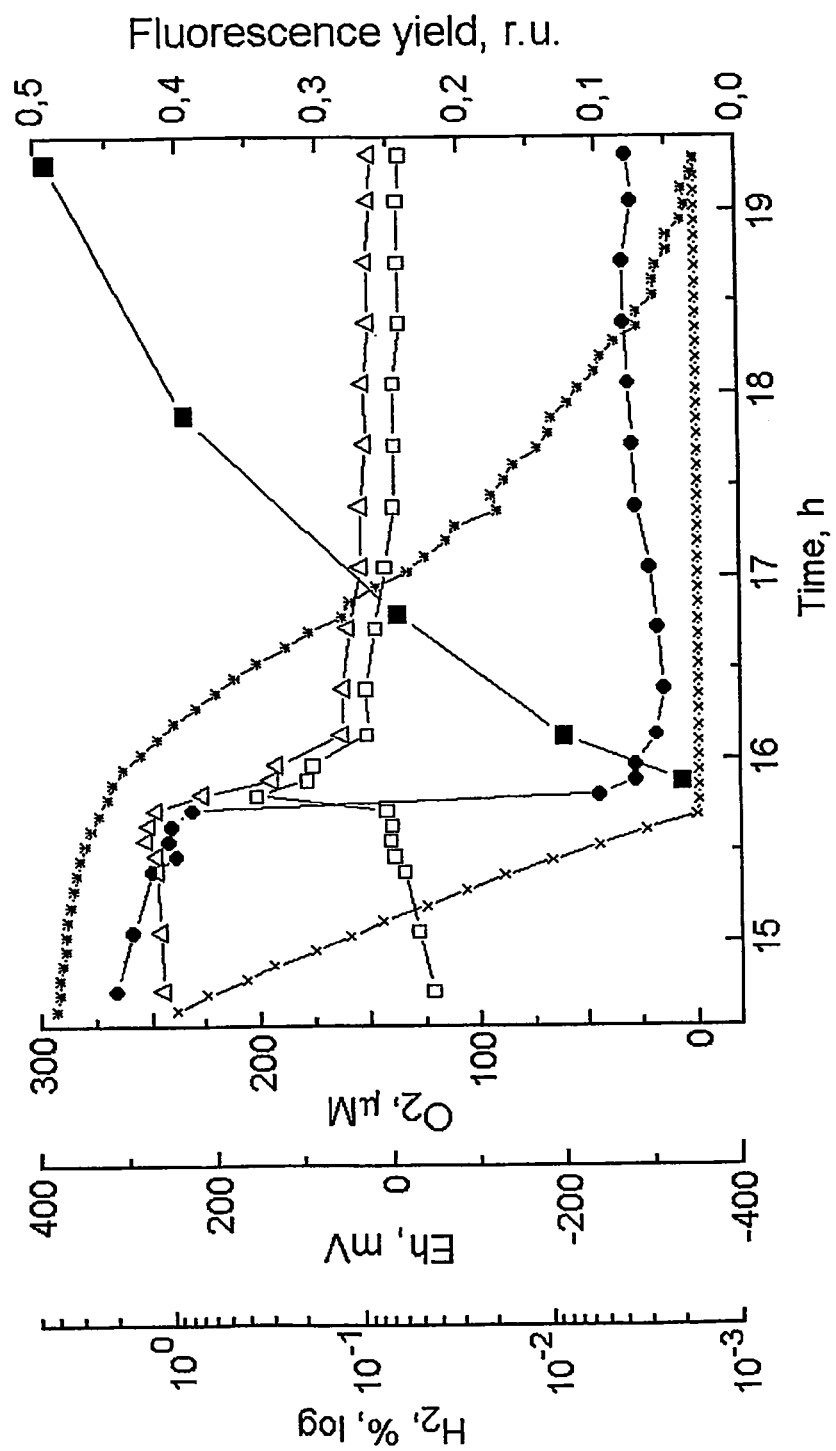

FIG. 3 is a graph showing in situ fluorescence parameters $F_t$ (open squares), $\Delta F/F_m'$ (solid circles), and $F_m'$ (open triangles), as well as $pO_2$ (crosses), $E_h$ (stars) and $H_2$ content in the gas phase of culture vessel (solid squares) in illuminated, sulfur-deprived, *C. reinhardtii* during the transition of the algae from aerobic to anaerobic conditions. Incubation in sulfur-deprived medium started at 0 h.

Figure 4:
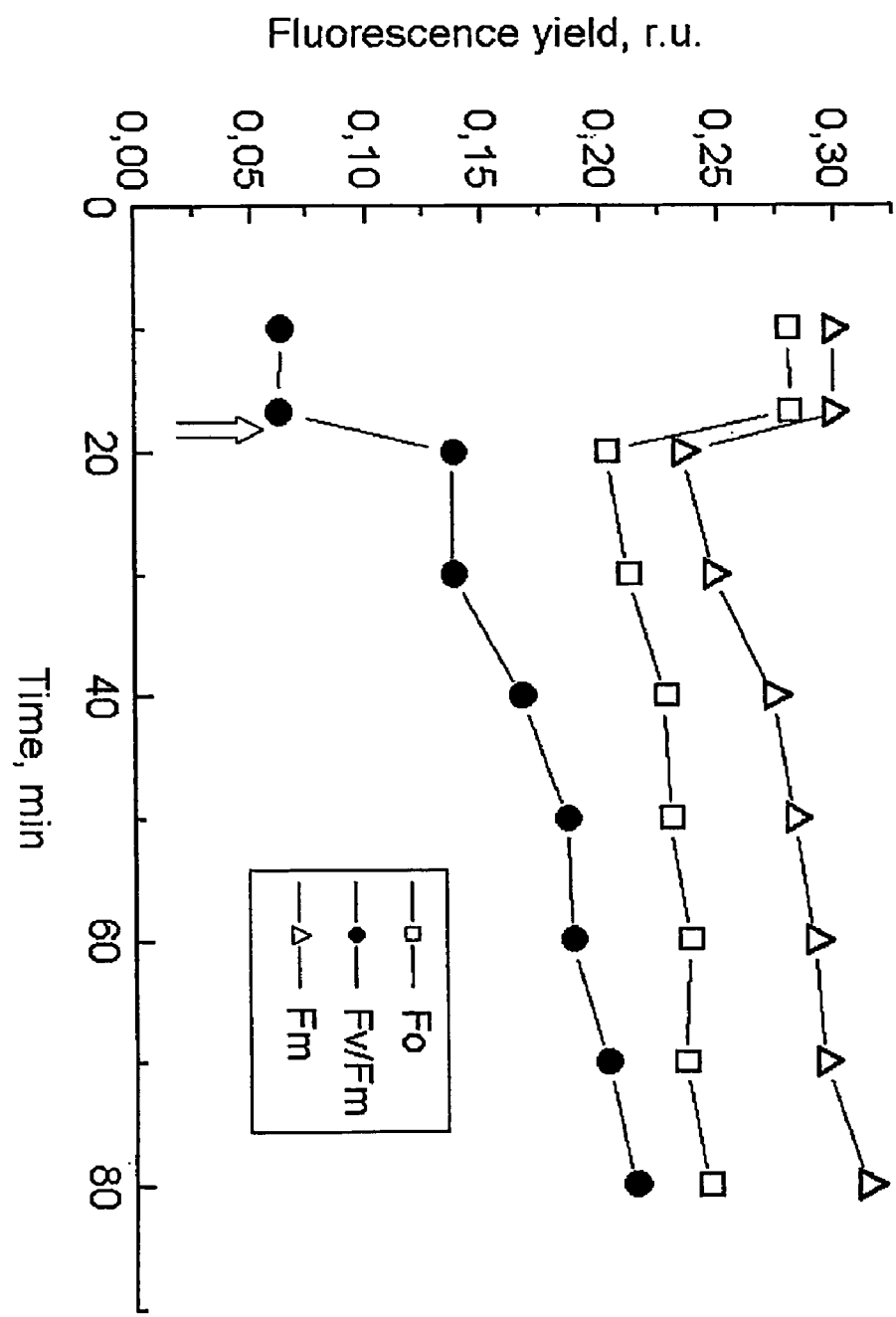

FIG. 4 is a graph showing changes in chlorophyll fluorescence parameters recorded in a dark-adapted algal sample, which was removed anaerobically from a culture vessel 22 hours after the beginning of $H_2$ production. After 18 minutes of dark adaptation, the algal sample was aerated (arrow). $F_0$ (open squares), $F_m$ (open triangles), and $F_v/F_m$ (solid circles) were monitored periodically as a function of time after removal from the culture vessel.

Figure 5:
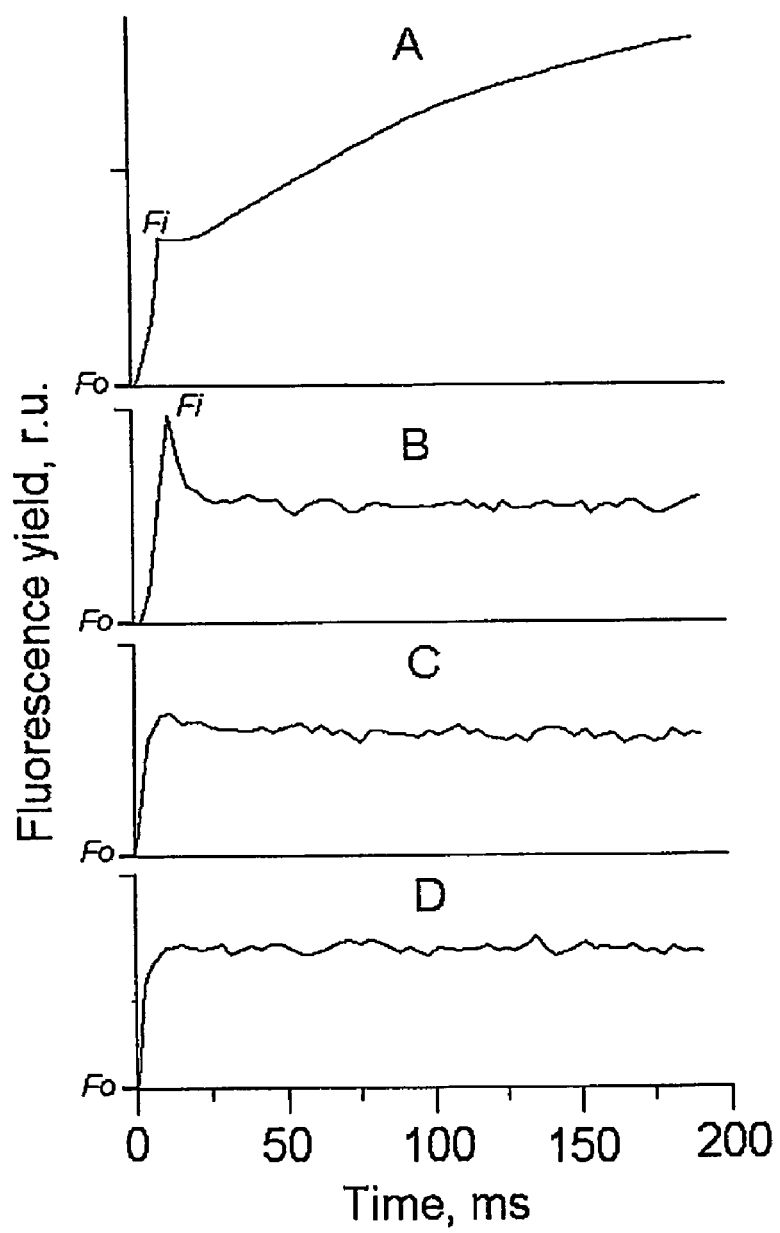

FIG. 5 is a graph showing chlorophyll fluorescence induction curves in control algae at the start of sulfur deprivation (A) and in cells removed from a culture vessel anaerobically after 22 hours of $H_2$ production (B, C, D). (B) Fluorescence kinetics were recorded while the cells were illuminated with saturating light after a 10-minute period of dark adaptation. (C) Same as (B) except far red light ($\lambda$~735 nm) was turned on for one second prior to the measurement. (D) Same as (B) except that the sample was aerated just prior to measurement. The $F_0$ level occurs at time zero.

DETAILED DESCRIPTION OF PREFERRED EMBODIMENT OF INVENTION

*Chlamydomonas reinhardtii* strain Dangeard C137+ was grown in Tris-acetate-phosphate (TAP) medium (pH, 7.0) under continuous cool-white fluorescent light. Late-log cells were pelleted three times by centrifiguation and re-suspended in the same medium, from which inorganic sulfure (TAP-S) was omitted. The cells were incubated under continuous fluorescent illumation (200-250 $\mu E\ m^{-2}\ s^{-1}$ PAR) in cylindrical reactor vessels (600 ml) with a rotating glass rod and Teflon impellers for mixing. A magnetic bar was attached at the bottom of the rod to couple it to an external stirring motor, and the rate of mixing was 60-80 rpm. The vessels were sealed using a silicon stopper with an outlet tube inserted through it for gas collection. The gas produced by the cells was collected in an inverted graduated glass cylinder by water displacement.

To determine the precise moment of $H_2$-photoproduction onset, we measured the percentage of $H_2$ contained in the gas phase (~7 ml) on the top of the vessel immediately after anaerobiosis by gas chromatography. The dissolved $O_2$ and redox potential of the medium were also measured. Chlorophyll concentrations were then obtained spectrophotometrically in 95% ethanol cell extracts. The capacity for respiratory $O_2$ consumption was measured with a Clark electrode at 25° C. under aerobic conditions (17% or 170 $\mu M$ $O_2$) after removing the samples from the culture vessel and equilibrating them with air for 5 minutes.

Chlorophyll fluorescence measurements were obtained with a portable PAM-2000 fluorometer using the weak modulated pulse-probe (Pulse-Amplitude-Modulation [PAM]) method. In situ measurements of fluorescence yield ($\lambda$>710 nm) were done with an optical fiber probe affixed closely onto the surface of the illuminated glass reactor vessel. The measurements were recorded every 15 minutes over the total period of sulfur deprivation. A 0.8 s saturating actinic excitation pulse ($\lambda$<710 nm, 1200 $\mu mol \cdot m^{-2} \cdot s^{-2}$ PAR) from an 8V/20 W halogen lamp was applied on top of weak modulated probe flashes (3 $\mu s$ pulses from a 655 nm light-emitting diode (LED) at frequencies of 600 Hz or 20 kHz.) for FIGS. 2-4, whereupon the following parameters were recorded: (a) $F_0$, the fluorescence yield of dark-adapted cells measured only in the presence of weak probe flashes; (b) $F_m$, the fluorescence yield of the same cells, following the application of the saturating actinic pulse; (c) $F_t$, the fluorescence yield of the cells, exposed to the ambient, steady-state illumination from fluorescence lamps or natural lighting in the reactor vessels, measured with the weak probe flashes; and (d) $F_m'$, the fluorescence yield of illuminated cells, as in (c), following application of the saturating actinic pulse. The efficiency of photochemical conversion of absorbed light energy (the photochemical activity) in PSII was calculated both after dark adaptation, where $F_v/F_m = (F_m - F_0)/F_m$, and under steady-state actinic light illumination, where $\Delta F/F_m' = (F_m' - F_t)/F_m'$. The kinetics of fluorescence induction was also measured with the PAM-2000 fluorometer. Samples were removed anaerobically from the reactor vessel and placed into a transparent plastic cuvette hermetically sealed with a stopper. Following a 10-minute dark, anaerobic adaptation period, the samples were illuminated with weak modulated probe flashes as above and actinic light (655 nm, 250 $\mu mol \cdot m^{-2} \cdot s^{-1}$ PAR from a LED array for 2 s), and the kinetics of fluorescence induction were measured at $\lambda$>710 nm (FIG. 5).

As mentioned above the sulfur-deprivation process involves $O_2$-production, $O_2$-consumption, anaerobic-adaptation, $H_2$-production and termination phases. These phases proceed over different periods of time, depending on the residual sulfur concentration (at the time of sulfur removal), chlorophyll and biomass content in the culture, pH of the culture medium, and other factors. This is why the beginning of the anaerobic phase is observed at different times after sulfur-deprivation in different experiments. The observed changes in cell parameters during the sulfur-deprivation process (excluding FIGS. 2 and 3) are expressed relative to the indicated physiological stage of the cultures.

One of the most critical questions about the mechanism of $H_2$ photoproduction in sulfur-deprived systems is the identification of the source of the electrons for gas production. The electrons could come from storage products or from water (i.e., electrons from water are transported from PSII to PSI), with subsequent reduction of ferredoxin and hydrogenase.

FIG. 1 shows the addition of DCMU (a potent inhibitor of electron flow at the level of $Q_B$ [the secondary PSII quinone acceptor] on the reducing side of PSII) to a culture, after $H_2$ gas production has started, abruptly decreases the rate of gas production by 80%. This demonstrates that most of the electrons from $H_2$ production are coming from water and is consistent with the fact that large amounts of $H_2$ are only produced in the light. The direct involvement of PSII-catalyzed water oxidation activity by sulfur-deprived cells was further investigated using PAM fluorescence techniques.

During the $O_2$-production and consumption phases of sulfur deprivation (the first 15 hours in the experiment shown in FIG. 2A), the Chl concentration was set at 11 $\mu g/ml$ at the beginning of the experiment, and the in situ-monitored fluorescence parameter, $F_m'$, did not change significantly. However, since the fluorescence parameter, $F_t$, slowly increased during this same period, the photochemical activity of PSII ($\Delta F/F_m'$), declined from 0.57 in the middle of the $O_2$-production phase to 0.44 at the end of the $O_2$-consumption phase (FIG. 2A). The observed changes in $F_m'$, $F_t$ and $\Delta F/F_m'$ reflect the existence of long-lived inactive states apparently generated in the $Q_B$-non-reducing centers of PSII. In fact, if samples of the algal suspension were removed aerobically from the culture vessels at the end of the $O_2$-consumption phase and dark-adapted for different periods of time, the fluorescence parameters, $F_0$ and $F_m$, and the fluorescence induction curves did not change significantly during a 40-minute incubation period (data not shown). This suggests that the $Q_B$-non-reducing state of PSII is long-lived in the dark once it is established.

The results are consistent qualitatively with previous observations showing that the capacity for $O_2$ production by PSII, the amount of light-reducible $Q_A^-$, (reduced form of the primary PSII quinone acceptor) and the rate of electron transport from PSII and PSI decrease during sulfur deprivation. However, it is noteworthy to point out that the experiments of Wykoff et al. and Melis et al. were done by removing samples from a photobioreactor and assaying for $O_2$ evolution under aerobic conditions, whereas our results are from in situ measurements.

FIG. 2A also shows that, in this experiment at 15 and 16 h after the start of sulfur deprivation, there was a rapid (<5 min) reduction of the in situ-measured photochemical yield of PSII ($\Delta F/F_m'$) from 0.4 to 0.1, which reflects a rapid down-regulation of PSII photochemical activity at this time. The loss of photochemical activity was due both to a rapid reduction in $F_m'$ and a rapid increase in $F_t$. It is important to note that in FIG. 3 (an expanded view of data from FIGS. 2A and B) the observed rapid reduction of PSII photochemical activity ($\Delta F/F_m'$) began at the exact time that the $O_2$ concentration in the culture suspension reached zero. The redox potential of the culture medium also started to decline around this time (FIGS. 2B and 3) but not nearly so fast as the $O_2$ concentration and PSII photochemical activity. At about one hour of anerobiosis, the PSII photochemical activity dropped to a minimum value (0.05). After that point, it gradually increased over the next 2 hours and reached a maximum value of 0.085 (FIGS. 2A and 3). No additional large changes were observed over 20 more hours of anerobiosis and $H_2$ production. If at this point (21 h after the beginning of anaerobiosis), an algal sample was removed anaerobically from the reactor vessel and placed into an anaerobic cuvette for 18 minutes in the dark, the PSII activity ($F_v/F_m$) of the dark-adapted cells increased rapidly from 0.07 to 0.14 when the cell suspension was subsequently aerated (FIG. 4). Following the aeration, the $F_v/F_m$ ratio increased slowly up to a value of 0.22 after an additional hour of aerobic incubation. This clearly demonstrates that the rapid in situ anaerobic inactivation of PSII photochemical activity is partially reversible by $O_{2-}$ in contrast to the slower aerobic inactivation of PSII observed during the $O_{2-}$ consumption stage of sulfur deprivation.

Volumetric measurements of $H_2$ gas accumulation, such as those presented in FIG. 2B, do not give the exact time of the start of $H_2$ photoproduction. To determine the exact onset of $H_2$ production, we measured the concentration of $H_2$ in the gas phase of the reactor vessel (FIG. 3). Trace quantities of $H_2$ (0.002%) were detected as early as 10 minutes after the onset anerbiosis. This is reflected at the point where the decrease in The $\Delta F/F_m'$ slows dramatically. The rate of $H_2$ accumulation in the gas phase increased from 0.04 µl of $H_2$ per minute within the first 10 minutes of anaerobiosis up to 1.0 µl per minute at the end of the second hour of anaerobiosis. This was accomplished by a moderate increase in the $\Delta F/F_m'$ value. Gas accumulation in the inverted graduate cylinder started after about 4 h of anaerobiosis (FIG. 2B), and the rate of $H_2$ accumulation was constant until at least 22 h after the beginning of anaerobiosis. These results suggest that the algae actually start to produce $H_2$ very shortly after the establishment of anaerobiosis. Apparently it takes a couple of hours to saturate the algal suspension with $H_2$ (the solubility of $H_2$ in water is 17 ml per 1 at 30° C.) and then build up enough gas pressure to displace the water in the gas-collection system. We show earlier that, under different initial conditions of cell cultivation and/or less accurate measuring conditions, the in situ measured photochemical yield of PSII drops to zero after the rapid decrease in photochemical yield. In the current study the observed recovery or up-regulation of PSII activity under anaerobic conditions correlates with the onset of $H_2$ production. This correlation confirms that PSII, and consequently residual water-splitting function, is the main source of electrons of $H_2$ production under these conditions.

As to the actual mechanisms responsible for the observed in situ changes in PSII activity in sulfur-deprived cultures, the initial slow inactivation of PSII capacity is believed to be due to the decreased ability of the cells to replace photo-damaged D1 protein, thus leading to the accumulation of $Q_B$-non-reducing PSII centers that cannot produce $O_2$. These changes result in the establishment of anaerobic conditions in the reactor vessel in the light.

In addition to the slow inactivation of PSII capacity, we demonstrate that a new, rapid down-regulation of PSII photochemical activity occurs just as the culture becomes anaerobic (FIGS. 2 and 3). This rapid down-regulation is not accompanied by a proportional loss of PSII capacity as measured by the capability of PSII to accumulate $Q_A$-or to evolve $O_2$ when the cells are exposed to aerobic conditions [FIG. 4]. It is believed that the rapid in situ PSII down-regulation is a response of the algae to the over-reduction of the plastoquinone (PQ) pool, which must accompany the establishment of anaerobiosis. Since there is no $O_2$ to reoxidize the PQ pool under anaerobic conditions and since PSI cannot further dispose of electrons from the pool (the hydrogenase is not active yet and there is little rubisco to utilize photosynthetically-generated electrons), PSII activity is reversibly down-regulated. A similar mechanism, but slower rate has been used to explain the irreversible loss of PSII activity in eukaryotic algae following exposure to high temperatures or when deprived of nutrients other than sulfur.

The evidence presented in FIG. 5 supports our suggestion that rapid down-regulation of PSII is induced by over-reduction of the PQ pool under anaerobic conditions. It is known that the rise from $F_0$ to the $F_i$ level on the fluorescence induction curve corresponds to the portion of PSII centers that are unable to reduce $Q_B$. A control, aerobic algal sample, removed from the aerobic culture vessel at the start of sulfur deprivation (see FIG. 2), was examined first. In this sample (FIG. 5A), the $F_i$ peak is followed by a slower rise of florescence to the—maximum level, and this reflects the reduction of the PQ pool. In contrast, fluorescence-induction curves recorded anaerobically from anaerobic, dark-adapted cells, 22 h after the start of anaerobic phase (FIG. 5B), had a pronounced $F_i$ peak but completely lacked a slow rise phase. The lack of the slow rise indicates that the PQ pool cannot be further reduced under these conditions. Accordingly, the $F_i$ peak disappeared if the algal suspension was pre-illuminated with far red light (FIG. 5C) or aerated (FIG. 5D) prior to recording the fluorescence kinetics. In the former case, the PQ pool was oxidized by PSI, which preferentially absorbs far red light, and in the latter it was oxidized by $O_2$ itself. The loss of the distinct $F_i$ peak occurs because oxidation of a small fraction of the PQ pool under these conditions reoxidizes $Q_B$ and this lowers the $F_i$ level to that of the steady-state value on this time scale. Under anaerobic conditions, reduction of the PQ pool occurs by residual photosynthetic electron transfer and/or by the transfer of reductants from anerobic substrate degradation in the chloroplast stroma to the PQ pool through the NAD(P)H-PQ oxidoreductase. In fact, the existence of such reductant transfer in our samples is confirmed by incomplete (80%) suppression of $H_2$ production after the addition of DCMU (FIG. 1).

The consumption of photosynethically produced $O_2$ during the $H_2$-production phase is essentially for maintaining the culture medium anaerobic for the operation of the hydrogenase. Oxygen consumption in C. reinhardtii is catalyzed by three main oxidases: (a) the chloroplast PQ-oxidase; (b) the mitochondrial cytochrome c-oxidase; and (c) the mitochondrial alternative oxidase. The existence of the respiratory electron transport process, chlororespiration, occurring in the chloroplasts of green algae explains the effect of respiratory inhibitors on chlorophyll fluorescence transients. The chlororespiratory chain allows the transfer of reductants (NADPH), generated by substrate degradation in the chloroplast stroma, to the PQ pool via the NAD(P)H-PQ oxidoreductase.

The PQ pool is further oxidized by dissolved $O_2$ through the action of PQ-oxidase. In the mitochondria, NADH and $FADH_2$ generated by the Krebs Cycle serve as the source of electrons for a membrane-bound electron transport chain with $O_2$ as the final electron acceptor. The cytochrome oxidase transduces the production of 3 ATP molecules per pair of electrons transported. The alternative oxidase, on the other hand, is actually active under conditions that require less ATP/NADH since its operation generates only 2 ATP/pair of electrons. In both cases, $O_2$ is the terminal electron acceptor. The mitochondrial cytochrome oxidase in *C reinhardtii* is inhibited by KCN, carbon monoxide, and sodium azide, while the alternative oxidase is specifically affected by salicylic hydroxamic acid (SHAM). The putative chloroplast PQ oxidase, on the other hand, is not inhibited by SHAM and only slightly affected by KCN. By measuring the influence of two inhibitors, KCN and SHAM, on the rates of dark respiration, we tried to estimate the relative contributions of each of the three oxidases at different times after sulfur deprivation. The actual contributions of the three oxidases to the scavenging $O_2$ in situ depend on many factors such as their relative $K_M$'s for $O_2$ and the rate of diffusion of $O_2$ from the chloroplast to the mitochondria. Thus, the inhibitor studies that follow may not directly reflect the actual situation in the photobioreactor, but they do indicate that changes in the relative contribution of the three oxidases occur over the course of sulfure deprivation.

Table 1 shows that sulfur-deprivation gradually inhibits the rates of dark respiration in *C. reinhardtii* over a 100-h incubation period.

TABLE I

| Phase of Sulfur depletion | Rate of respiration ($\mu$moles $O_2$/mg $Chl^{-1} \times h^{-1}$) | % KCN inhibition (% CO) | % SHAM inhibition (% AO) | Putative % PQ-oxidase (% CR) |
| --- | --- | --- | --- | --- |
| Start of sulfur depletion | 30 | 60 | 25 | 15 |
| Start of anaerobic phase | 28 | 16 | 0 | 84 |
| Start of $H_2$ production phase | 22 | 36 | 13 | 51 |
| During $H_2$ production | 18 | 8 | 38 | 54 |
| End of $H_2$ production | 6 | 17 | 100 | 0 |

Contributions to the mitochondrial cytochrome oxidase [CO], mitochondrial alternative oxidase [AO], and chlororespiration [CR] to the total respiration rate of *C. reinhardtii* cells are also shown during sulfur-deprivation. Respiration rates were measured with cells taken from the bioreactor at different times after sulfur depletion, equilibrated with air and incubated with the inhibitors for 5 min. Rates were measured when the $O_2$ concentration in the medium was 17% $O_2$. Final concentrations of KCN and SHAM were 5 mM and 4 mM, respectively.

At the start of sulfur deprivation, the cytochrome oxidase and the alternative oxidase contributed, respectively, about 60 and 25% to the overall respiration capacity of the cells measured in the presence of 17% (170 $\mu$M) $O_2$. The remainder (about 15%) appears due to the activity of the chloroplast PQ-oxidase (Table I, last column),; however, it should be noted that the specificity of the inhibitors is not 100%. At the start of the anaerobic phase, the activity of the two mitochrondial oxidases decreased substantially to 16 and 0% of the total respiration capacity, respectively. This indicates a shift from mitochondrial respiration to chlororespiration. The shift towards chlororespiration was coupled to the shut-down of electron transport from PSII (FIGS. 2 and 3) caused by the over-reduction of the PQ pool, and the complete removal of $O_2$ from the sulfur-deprived culture medium. Once $H_2$ evolution started and accompanying up-regulation of PSII began, photosynthetically-generated $O_2$ appeared to be consumed equally by the mitochondrial (49%) and chloroplast (51%) oxidases (see Table I). During the $H_2$-production phase, the contribution of the chlororespiratory PQ oxidase remained unchanged. However, over the same period of time, the contribution of the mitochondrial cytochrome oxidase declined dramatically while the alternative oxidase increased. At the end of the $H_2$-production phase, the mitochondrial respiratory activity was due mostly to the alternative oxidase. Thus, the inhibitor studies in Table I support the active role of chlororespiration in maintaining the anaerobic conditions in the chloroplast required for $H_2$ photoproduction, and they are also consistent with the idea that the alternative oxidase is expressed preferentially under stress conditions. This differential activity has also been observed in phosphate- or nitrogen-depleted *C. reinhardtii* and tobacco cells.

From FIGS. 2 and 3, it can be seen that the sharp down-regulation of PSII photochemical activity is reflected in an increase in $F_t$, which is the result of a sharp increase in the number of active PSII centers that are unable to reduce $Q_B$. Decreases in $F_m'$ are due to increases in non-photochemical quenching of PSII, and one of the known mechanisms responsible for non-photochemical quenching is the generation of a $\Delta$pH gradient across the photosynthetic membrane. These fluorescence studies show that the sharp drop in $F_m'$ at the time that $O_2$ concentration in the culture reaches zero occurs at approximately the same time that the PQ pool becomes over-reduced. Since the oxidized PQ pool is the source of reductant for chlororespiration, the inhibitor studies (Table I) appear to indicate that the chlororespiratory pathway begins to make a major contribution to $O_2$ removal from the culture at about the same time. It therefore appears that the rapid decrease in PSII photochemical is also due to the enhancement of chlororespiration, accompanied by the generation of a gradient. The increase in $\Delta$pH appears to be the main functional mechanism of non-photochemical quenching under the conditions responsible for the observed drop in $F_m'$.

The observed up-regulation of PSII activity that follows the establishment of anaerobiosis in the culture vessel (FIGS. 2B and 3) appears to be the result of induction of reversible Fe-hydrogenase enzyme activity, which catalyzes ferredoxin-dependent reduction of protons and releases $H_2$. In fact, the hydrogenase provides a sink for electrons generated either by light-catalyzed water oxidation or by metabolic oxidation of endogenous substrates, and its activity results in the partial oxidation of the intermediate photosynthetic carriers, including the PQ pool. Hence under anaerobic conditions, $H_2$ production by sulfur-deprived cells allows the system to retain a fraction of the PSII reaction centers in a photochemically active state. The $O_2$ evolved under these conditions, as indicated, appear to be consumed in part by chlororespiration or by storage-product degradation linked to mitochondrial respiratory processes that utilize both the cytochrome oxidase and the alternative oxidase as the final electron acceptors.

In the context of the inventive process, it is important to note that, if only the redox potential is measured without measuring the dissolved $O_2$ concentration, it is not possible to know exactly when the system goes anaerobic; however, the invention process measures the $O_2$ concentration in the culture at the same time that the fluorescence is measured to ascertain the exact time the system goes anaerobic (required for $H_2$ production). More specifically, the exact time the system goes anaerobic is when the fluorescence ($F/F_m'$) starts its abrupt drop, and this is the point where PSII activity is down-regulated.

In summarization, it is seen that changes of PSII activity in *C. reinhardtii* cells deprived of inorganic sulfur are characterized by complicated dynamics during the course of cell adaptation to the nutrient stress. We therefore conclude that (a) the redox state of the PQ pool is the primary factor in regulating the activity of any remaining PSII water-splitting capacity by controlling the PSII photochemical activity in the algae during all phases of sulfur deprivation and (b) most of the electrons used directly for $H_2$ gas production come from water. Thus, the redox state of the PQ pool depends on the relationship between the rates of photosynthesis, chlororespiration, respiration, and $H_2$ production.

The invention claimed is:

1. An in situ fluorescence method for external on-line monitoring of the physiological state a sulfur-deprived algal culture inside a closed photobioreactor system to ascertain the culture's production of $H_2$ under sulfur depletion, comprising:
   a) providing a sample of sulfur-deprived algal culture containing photosynthetic components;
   b) illuminating said sample with artificial or natural illumination;
   c) determining the onset of $H_2$ photoproduction by measuring the percentage of $H_2$ in a produced gas phase at multiple times to ascertain the point immediately after the anerobiosis subsequent to the physiological phases of $O_2$ production and $O_2$ consumption sequence to obtain data regarding $H_2$ production as a function of time; and
   d) determining any abrupt change in the following three in situ fluorescence parameters:
      i) an abrupt increase in $F_t$ (the steady-state level of chlorophyll fluorescence in light adapted cells);
      ii) an abrupt decrease in $F_m'$ (the maximal saturating light induced fluorescence level in light adapted cells); and'
      iii) a precipitous and abrupt decrease in $\Delta F/F_m' = (F_m' - F_t)/F_m'$ (the calculated photochemical activity of photosystem II (PSII)) that signals the full reduction of the plastoquinone pool between PSII and PSI, which indicates the start of anaerobic conditions that in turn induces the synthesis of the hydrogenase enzyme required for subsequent $H_2$ production, and thereafter slowing down of the abrupt decrease and partial recovery of $\Delta F/F_m'$ signals at least partial oxidation of the plastoquinone pool as the main factor to regulate $H_2$ production under sulfur depletion.

2. The method of claim 1 wherein said algal culture is any oxygenic photosynthetic microorganism that has a hydrogenase.

3. The method of claim 2 wherein said oxygenic photosynthetic microorganism that has a hydrogenase is green algae.

4. The method of claim 3 wherein said green algae is selected from the group consisting of *Chlamydomonas reinhardtii, Scenedesimus obligus* and *Chlorella vulgaris*.

5. The method of claim 4 wherein said green algae is *Chlamydomonas reinhardtii*.

6. The method of claim 5 wherein said abrupt increase in $F_t$ is determined using a fluorometer employing a weak modulated pulse-probe fluorescence method.

7. The method of claim 5 wherein said in situ measurement of fluorescence is at or about $\lambda > 710$ nm.

8. The method of claim 7 wherein said in situ measurement of fluorescence is performed with an optical fiber probe affixed onto a surface of an illuminated glass containing fluorescence excited sample or alternatively with a lens system.

9. The method of claim 7 wherein said in situ measurement of fluorescence is performed with a fluorometer set close to the edge of a bioreactor.

10. The method of claim 7 wherein said in situ measurement of fluorescence is performed with a lens set close to the edge of the bioreactor.

11. The method of claim 8 wherein a saturated actinic excitation pulse is applied on top of a weak modulated probe pulse.

12. The method of claim 11 wherein said saturated actinic excitation pulse is a 0.8 s pulse (about $\lambda < 710$ nm, 1200 $\mu mol \cdot m^{-2} \cdot s^{-2}$ PAR) from an 8 V/20W halogen lamp.

13. The method of claim 11 wherein actinic light is about 655 nm, 250 $\mu mol \cdot m^{-2} \cdot s^{-1}$ PAR from a LED array for about 2 s for fluorescence induction.

14. The method of claim 12 wherein said saturating actinic excitation pulse is applied on top of a weak modulated probe that flashes at about 3 $\mu s$ pulses from a 655 nm light-emitting diode at frequencies of from about 600 Hz or 20 kHz.

15. The method of claim 14 wherein efficiency of photochemical conversion of absorbed light energy in PSII is calculated after dark adaptation, where $F_v/F_m = (F_m - F_o)/F_m$.

16. The method of claim 14 wherein efficiency of photochemical conversion of absorbed light energy in PSII is calculated under steady-state actinic light illumination, where $\Delta F/F_m' = (F_m' - F_t)/F_m'$.

* * * * *